United States Patent

Pressman et al.

[11] Patent Number: 5,284,964
[45] Date of Patent: Feb. 8, 1994

[54] METHOD FOR MAKING AROMATIC CARBONATES

[75] Inventors: Eric J. Pressman, East Greenbush; Joseph A. King, Jr., Schenectady, both of N.Y.

[73] Assignee: General Electric Company, Schenectady, N.Y.

[21] Appl. No.: 929,862

[22] Filed: Aug. 17, 1992

[51] Int. Cl.$^5$ .............................................. C07C 68/04
[52] U.S. Cl. ................................ 558/260; 558/274; 558/277
[58] Field of Search ................ 558/260, 274, 277

[56] References Cited

U.S. PATENT DOCUMENTS 4,761,467 8/1988 Bhattacharya ..................... 558/274

FOREIGN PATENT DOCUMENTS 350700 7/1988 European Pat. Off. ............ 558/274

Primary Examiner—Mary C. Lee
Assistant Examiner—Jacqueline Haley
Attorney, Agent, or Firm—William A. Teoli; William H. Pittman

[57] ABSTRACT

A method is provided for making aromatic carbonates, such as diphenyl carbonate by the carbonylation of an aromatic hydroxy compound, such as phenol in the presence of a palladium catalyst and an organic cocatalyst, such as a terpyridine compound.

4 Claims, 1 Drawing Sheet

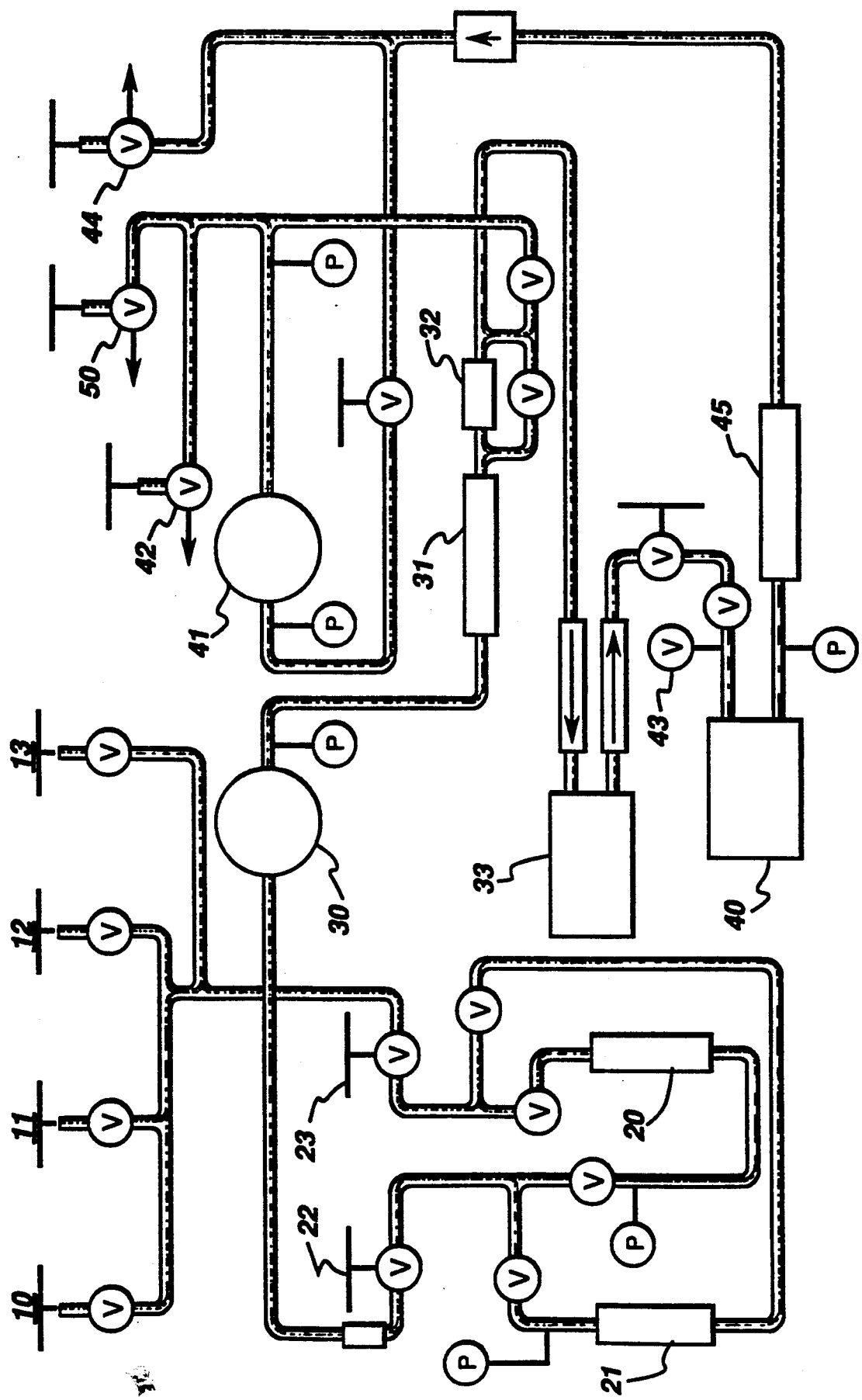

METHOD FOR MAKING AROMATIC CARBONATES

CROSS REFERENCE TO RELATED APPLICATIONS

Reference is made to copending applications 07/929,749, 07/929,816 and 07/929,860 filed concurrently herewith, and copending application Ser. No. 07/906,681, filed Jul. 7, 1992.

BACKGROUND OF THE INVENTION

The present invention relates to a method for making aromatic organic carbonates such as diphenyl carbonate by effecting reaction between an aromatic organic hydroxy compound, such as phenol, and carbon monoxide and oxygen in the presence of an effective amount of a palladium carbonylation catalyst. More particularly, the present invention relates to the carbonylation of an aromatic organic hydroxy compound utilizing an organic cocatalyst, such as a terpyridine in combination with the palladium carbonylation catalyst.

Procedures for making diorganic carbonates are shown by Hallgren, U.S. Pat. Nos. 4,361,519 and 4,410,464, utilizing a molecular sieve as a drying agent for the water formed during the reaction. A procedure for making aromatic organic carbonates by catalytic carbonylation is shown by Japanese patent 01,165,551. Aromatic organic carbonates are of particular interest to thermoplastic manufacturers, since they offer an alternative non-phosgene route to aromatic polycarbonates by melt transesterification. A procedure for making aromatic organic carbonates using an organic solvent, such as methylene chloride, is shown by Chalk, U.S. Pat. No. 4,187,242. Reference also is made to T. C. Chang in EPA 8911158.8, Jun. 26, 1989, and EP350-700-A, utilizing a divalent or trivalent manganese salt, or cobalt (II) salt in combination with hydroquinone and a palladium catalyst, to catalyze the conversion of an aromatic organic hydroxy compound, such as phenol, to an aromatic organic carbonate. U.S. Pat. No. 4,218,391, Romano et al employ a copper salt to prepare organic esters of carbonic acid. Attempts to use such catalyst with aromatic organic hydroxy compounds, such as phenol, under constant flow conditions have been found to provide unsatisfactory results with respect to % carbonate yields and % carbonate selectivity as compared to the use of aliphatic hydroxy compounds, such as methanol, in preparing aliphatic carbonates under substantially the same conditions.

In application EP350-700-A and copending application Ser. No. 07/906,681, carbonylation of aromatic organic hydroxy compound was achieved utilizing a divalent or trivalent manganese salt or cobalt (II) salts and organic cococatalyst such as hydroquinone or benzoquinone in combination with a palladium catalyst. Although the aforementioned cocatalyst system provides improved yields of aromatic organic carbonate as a result of the carbonylation of aromatic organic hydroxy compounds, organic cocatalyst, such as benzoquinone has to be utilized in the range of 10-40 equivalents per equivalent of palladium, to show a reasonable rate of aromatic organic carbonate production. In addition it has been found that benzoquinone organic cocatalyst based systems are often readily degraded resulting in the production of color bodies and reduced catalyst stability following exposure to ambient conditions. As a result it was not feasible to recycle palladium carbonylation catalyst used in the manufacture of aromatic organic carbonates at elevated conditions of temperature and pressure and there after allow the introduction of make-up aromatic organic hydroxy compound into the reactor under ambient conditions.

SUMMARY OF THE INVENTION

The present invention is based on the discovery that if certain heterocyclic amines, such as terpyridines or phenanthrolines are substituted for benzoquinone as the organic cocatalyst in combination with an inorganic cocatalyst to produce a palladium carbonylation catalyst, the resulting carbonylation catalyst has been found to be substantially more stable under ambient conditions following its use in aromatic organic carbonate production. In addition, these heterocyclic amines also have been found to provide carbonylation catalyst having substantially enhanced activity when used in place of benzoquinone as the organic cocatalyst. As a result, a significant advance is provided in aromatic organic carbonate manufacture by using carbonylation catalyst having enhanced activity and allowing the use of recycled palladium carbonylation catalyst with make-up aromatic organic hydroxy compound.

STATEMENT OF THE INVENTION

There is provided by the present invention, a method for making aromatic organic carbonate comprising effecting reaction at a temperature of about 60° C. to about 150° C. between aromatic organic hydroxy compound, carbon monoxide and oxygen in the presence of an effective amount of a palladium carbonylation catalyst comprising a substantially quinone free mixture of, (a) catalytically active palladium in the metallic or chemically combined state, (b) an inorganic cocatalyst selected from the class consisting of divalent, cobalt, manganese and copper compounds, trivalent cobalt, manganese and copper compounds which compounds are selected from the class consisting of salts, complexes with diketones, and complexes with carbon monoxide, (c) an organic cocatalyst selected from the class consisting of terpyridines, phenanthrolines, quinolines, isoquinolines, and (d) quaternary ammonium or quaternary phosphonium halide.

The palladium material useful as a catalyst can be in elemental form, or it can be employed as a palladium compound. Accordingly, palladium black or elemental palladium deposited on carbon can be used as well as palladium compounds, such as halides, nitrates, carboxylates, oxides and complexes involving such compounds such as carbon monoxide, amines, phosphines or olefins. The preferred palladium compounds are palladium (II) salts of organic acids including carboxylates with $C_{(2-6)}$ aliphatic acids. Palladium (II) acetate is particularly preferred. There is used in combination with the palladium catalyst, tetraalkylammonium halide or tetraalkylphosphonium halide, such as the chlorides and bromides and particularly the bromides. Alkyl groups of the alkyl ammonium halides are primary and secondary alkyl groups containing about 1-8 carbon atoms. Tetra-n-butylammonium bromide is particularly preferred.

Aromatic organic amines which have been found effective in the practice of the present invention as part of the transition metal catalyst are terpyridine compounds, such as 2,2':6',2"-terpyridine, 2,2':6',2"-4'-thiomethylterpyridine and 2,2':6',2"-4-terpyridine-N-oxide. In addition to terpyridine compounds, phenanthroline compounds also can be be used such as, 1,10-phenanthroline, 2,4,7,8-tetramethyl-1,10-phenanthroline, 4,7-diphenyl-1,10-phenanthroline and 3,4,7,8-tetramethyl-1,10-phenanthroline.

In forming aromatic organic carbonates, such as diphenyl carbonate, cobalt or manganese coumpounds such as divalent or trivalent compounds, for example, salts such as halides and carboxylates and complexes with amines, diketones and carbon monoxide have been found effective as inorganic cocatalysts. Cobalt (II) acetate is particularly preferred. It has been found that optimum selectivity i.e., optimizing the formation of aromatic carbonate and minimizing the formation of aromatic salicylate is achieved using the cobalt (II) catalyst.

An effective amount of the palladium catalyst is, for example, an amount sufficient to provide about 1 gram-atom of palladium, per 800–10,000 and preferably 2,000–5,000 moles of organic hydroxy compound. The other components of the palladium catalyst are, for example, per gram-atom of palladium, about 0.1–3 moles, and preferably about 0.3–1 moles of aromatic organic amine, about 0.1–5.0, preferably about 0.5–1.5 gram-atoms of cobalt, or manganese or copper and about 5 to 150 and preferably about 20–50 moles of the tetraalkylammonium or tetraalkylphosphonium halide.

Solid drying agents, such as molecular sieves, can be used to improve yields. In some instances, carbon dioxide also can be used as a dessicant as taught in copending application Ser. No. 07/503,404, filed Apr. 2, 1990.

In order that those skilled in the art will be better able to practice a preferred form of the present invention, reference is made to the drawing. The drawing shows a schematic of a gas flow reactor system for preparing aromatic organic carbonate capable of delivering in a continuous manner at a flow rate about 50 ml to 1000 ml and preferably about 300 ml to 600 ml per min, a mixture of carbon monoxide and oxygen maintained at a substantially constant molar ratio and partial pressures.

More particularly, there is shown at 10 a carbon monoxide gas inlet and at 11, an oxygen inlet. 12 is a manifold vent, and 13 is an optional inlet for a gas, such as carbon dioxide. The reaction mixture can be fed into a low pressure reservoir at 20, or a high pressure reservoir at 21 which can be operated at a higher pressure than the reactor for the duration of the run. At 22 there is shown a reservoir outlet and at 23 a reservoir inlet. The gas feed pressure can be adjusted to about 50 psi over the desired reactor pressure at a reducing pressure regulator at 30. The gas can be further purified in scrubber 31 and then fed into a mass flow controller at 32 to allow for the previously described flow rates. The reactor feed gas can be heated in an oil bath at 33 having appropriate conduit means prior to being introduced to the reactor at 40. The reactor pressure can be controlled through manipulation of a back pressure regulator at 41. The reactor gas effluent may be either sampled for further analysis at 42 or vented to the atmosphere at 50. The reactor liquid can be sampled at 43. 45 is a condenser. An additional vent at 44 can allow for further system control, but is typically closed during the gas flow reaction.

In the practice of one form of the invention, the palladium catalyst, co-catalyst package, and aromatic organic hydroxy compound are charged to the reactor. The reactor is sealed. Carbon monoxide and oxygen are introduced into an appropriate reservoir within proportions previously defined, until a suitable pressure such as 2800 psi is achieved.

Circulation of condenser water is initiated and the oil bath temperature can be raised to 100° C. Conduit between the oil bath and the reactor can be heated using heat tape to a suitable temperature such as 100° C. The mass flow bypass can be opened and an appropriate accumulator valve can be opened and the reducing pressure regulator can be used to adjust the pressure. The reactor pressure can be further adjusted by the back pressure regulator. The mass flow bypass can be closed and the flow can be adjusted using the mass flow controller. Agitation of the reaction ingredients can be initiated once the reactor temperature is raised sufficiently to minimize the presence of solids such as phenol. Upon reaching a desirable reactor temperature, such as 100° C., aliquots can be taken to monitor the reaction.

Upon completion of the reaction, the temperature of the reaction mixture can be reduced and the reactor pressure reduced to atmospheric to allow for the recovery of aromatic organic carbonate.

In order that those skilled in the art will be better able to practice the present invention, the following examples are given by way of illustration and not by way of limitation. All parts are by weight unless otherwise indicated.

Example 1

There was placed into a 300 ml 316 SS Parr autoclave, 56.44 g (600 mmol) of phenol, 1.61 g (5 mmol) of tetrabutylammonium bromide, 27 mg (0.12 mmol) of palladium diacetate, 21.2 mg (0.12 mmol) of cobalt diacetate and 14.4 mg (0.06 mmol) of 2,2':6,2"-terpyridine which may be referred to herinafter as "terpyridine". The reactor was sealed and flushed three times with carbon monoxide at 400 psi pressure. The reactor was then charged with oxygen at 110 psi and carbon monoxide at 590 psi at 30° C. The vessel was heated to 100° C. and the reaction mixture was stirred at about 500 rpm for the course of the reaction which included the heat-up and cool-down. Aliquots were taken at predetermined times to assess the amount of diphenyl carbonate which had been produced by GC analysis. Sampling of the reactor showed a diphenyl carbonate yield of 0.38% at 0.0 hr, 1.0% at 0.5 hr., 1.99% at 1.0 hr, 5.01% at 2.0 hrs, 14.41% at 5.0 hrs, and 17.03% at 7 hrs.

The same procedure was repeated except that other organic cocatalyst (OCC) were used in addition to a variation in the molar ratio of the OCC/Pd and a temperature between 100°–115° C. The following results were obtained:

TABLE 1

| Organic Co-Catalysts (OCC) | Moles OCC/Pd | % DPC 7 hr | Temperature |
|---|---|---|---|
| Terpyridine | 0.5 | 12.4 | 100° C. |
| Terpyridine | 0.5 | 17.0 | 115° C. |
| Terpyridine | 1.0 | 8.4 | 115° C. |
| Benzoquinone | 12.5 | 9.7 | 100° C. |
| DDD-phen* | 1.5 | 12.3 | 100° C. |
| 2,2'-Biquinoline | 1.0 | 15.6 | 100° C. |

*DDD-phen = 6,7-dihydro-5,8-dimethyldibenzo[b,1][1,10]phenanthroline

The above results show that the terpyridine cocatalyst of the present invention provides significantly improved yields of diphenyl carbonate as compared to the benzoquinone of the prior art which is utilized at a signficantly higher molar proportion to palladium.

Example 2

Into the flow reactor, as shown by the drawing, which was operated at a temperature of 115° C., there was added 59.4900 g (632 mmol) of phenol, 4.0840 g (12.67 mmol) of tetrabutylammonium bromide, 0.0562 g (0.3185 mmol) of cobalt diacetate, 0.0348 g (0.149 mmol) of terpyridine and 0.0674 g (0.300 mmol) of palladium diacetate which provided 501 ppm of palladium. There was also utilized 24.89 g of molecular sieves which had been activated during the previous 12 hours at 300° C. and which were contained in a perforated Teflon resin basket and mounted to the stir shaft above the liquid level of the reaction mixture. A gas mixture consisting of 92.9% carbon monoxide and 7.1% oxygen at 2800 psi was prepared in the reservoir and subsequently introduced into the reactor at a flow rate of 350 ml/min±0.10 ml/min. The reactor pressure was adjusted to 1600 psi.

Upon reaching a reactor temperature of 115° C., aliquots were taken periodically for GC analysis in order to quantify the amount of diphenyl carbonate produced. At 0.0 hr, the yield of diphenyl carbonate was 0.193 g (0.28%), at 0.50 hr, the yield of diphenyl carbonate was 1.86 g (2.75%), at 1.00 hr, the yield of diphenyl carbonate was 4.86 g (7.19%). After 3.5 hrs, the yield of diphenyl carbonate was 26.4 g (38.94%), at 5.00 hrs, the yield of diphenyl carbonate was 35.9 g (53.07%), at 6.00 hrs, the yield of diphenyl carbonate was 40.3 g (59.50%), and at 7.00 hrs, the yield of diphenyl carbonate was 42.9 g (63.34%). Other organic cocatalyst (OCC) were used in the range of from 0 to 20 moles per mole of palladium. In addition, the palladium catalyst was utilized over a range of between 134 ppm to 518 ppm while the temperature was varied between 100° C. to 115° C. The following results were obtained:

TABLE 2

| Organic Co-Catalyst (OCC) | Moles OCC/Pd | [Pd] (ppm) | Temp. (°C.) | % DPC 7 hr | % DPC 13 hr |
|---|---|---|---|---|---|
| None | 0 | 134 | 100 | 8.4 | — |
| Benzoquinone | 20 | 140 | 100 | 15.4 | 23.8 |
| 1,10-Phenanthroline | 1.4 | 145 | 100 | 13.9 | 22.0 |
| TMPhen* | 1.1 | 140 | 100 | 11.9 | 17.8 |
| 2,2'-Biquinoline | 0.96 | 143 | 100 | 12.9 | 24.1 |
| 1,10-Phenanthroline | 1.0 | 518 | 110 | 36.5 | — |
| 2,2':6',2''-Terpyridine | 0.5 | 501 | 115 | 63.3 | — |

*TMPhen = 2,3,7,8-Tetramethyl-1,10-phenanthroline

The above results show that under constant composition gas flow reactor conditions, terpyridine organic cocatalyst as well as the other organic cocatalyst of the present invention provide superior yields of diphenyl carbonate in terms of the OCC/Pd ratio used. Although benzoquinone was found to be an effective catalyst, it required a much larger molar ratio with respect to palladium compared to the other organic cocatalysts shown in Table 2. In addition, the benzoquinone was found to decompose readily under the conditions of the reaction as compared to the other organic cocatalyst shown above.

Although the above examples are directed to only a few of the very many variables which can be utilized in the practice of the method of the present invention, it should be understood that the present invention is directed to a much broader variety of palladium catalyst, organic cocatalyst and inorganic cocatalyst as set forth in the description preceding these examples.

What is claimed is:

1. A method for making aromatic organic carbonate in a reactor at elevated conditions of temperature and pressure from aromatic organic hydroxy compound in the presence of a palladium catalyst exhibiting enhanced stability as a recycled carbonylation catalyst at elevated conditions of temperature and pressure following its exposure to ambient conditions at the termination of an earlier carbonylation reaction, where the carbonylation catalyst having such enhanced stability allows the recovery of aromatic organic carbonate from the reactor under ambient conditions and the reintroduction of make-up aromatic organic hydroxy compound to the reactor under ambient conditions to provide the production of additional aromatic organic carbonate, which method comprises, (1) heating to a temperature between about 60° C. to about 150° C. at above atmospheric pressure, a mixture comprising aromatic organic hydroxy compound, carbon monoxide, oxygen and an effective amount of a palladium carbonylation catalyst comprising a quinone free mixture of,
      (a) catalytically active palladium in the metallic or chemically combined state,
      (b) an inorganic cocatalyst selected from the group consisting of divalent, cobalt, manganese and copper compounds, trivalent cobalt, manganese and copper compounds which compounds are selected from the group consisting of salts, complexes with diketones, and complexes with carbon monoxide,
      (c) a terpyridine cocatalyst, and
      (d) quaternary ammonium or quaternary phosphonium halide,
   (2) recovering aromatic organic carbonate from the mixture of (1) at ambient conditions and,
   (3) adding aromatic organic hydroxy compound to the resulting mixture of (2) under ambient conditions.

2. A method in accordance with claim 1, where the aromatic organic carbonate is diphenyl carbonate.

3. A method in accordance with claim 1 where the quaternary ammonium halide is tetra-n-butyl-ammonium bromide.

4. A method in accordance with claim 1 where the reaction is effected under either constant carbon monoxide and oxygen gas flow or batch conditions.

* * * * *